(12) United States Patent
Guida et al.

(10) Patent No.: US 6,448,003 B1
(45) Date of Patent: Sep. 10, 2002

(54) GENOTYPING THE HUMAN PHENOL SULFOTRANSFERBASE 2 GENE STP2

(75) Inventors: Marco Guida; Janice Kurth, both of San Diego, CA (US)

(73) Assignee: DNA Sciences Laboratories, Inc., Morrisville, NC (US)

( * ) Notice: Subject to any disclaimer, the term of this patent is extended or adjusted under 35 U.S.C. 154(b) by 0 days.

(21) Appl. No.: 09/328,174

(22) Filed: Jun. 8, 1999

Related U.S. Application Data

(60) Provisional application No. 60/088,710, filed on Jun. 10, 1998.

(51) Int. Cl.[7] .................. C07H 21/04; C12Q 1/68; C12P 19/34
(52) U.S. Cl. .............. 435/6; 435/91.2; 536/23.2; 536/23.5; 536/24.31; 536/24.33
(58) Field of Search .................... 536/21.31, 24.33, 536/23.5, 23.2; 435/6, 193

(56) References Cited

U.S. PATENT DOCUMENTS

| | | | | |
|---|---|---|---|---|
| 5,821,091 A | * | 10/1998 | Dolganov | 435/91.2 |
| 5,892,010 A | * | 4/1999 | Gray et al. | 536/23.1 |
| 5,922,617 A | * | 7/1999 | Wang et al. | 436/518 |
| 6,183,968 B1 | * | 2/2001 | Bandman et al. | 435/6 |
| 6,239,264 B1 | * | 5/2001 | Philippsen et al. | 536/23.1 |
| 6,265,561 B1 | * | 7/2001 | Weinshilboum et al. | 536/23.2 |

OTHER PUBLICATIONS

Hacia. Nature Genetics. 14: 441–447, Dec. 1996.*
Zhu et al. International Journal Biochem Cell Biology 28: 565–571, Dec. 1996.*
Her, C. NCBI Entrez Accession No. U34804 (1996).
Dooley et al., *Biochem. Biophys. Res. Comm.*, 228:134–140 (1996).
Gaedigk et al., *Genomics*, 40:242–246 (1987).
Her et al., *Genomics*, 33:409–420 (1996).
Reiter et al., *Clin. Pharmacol. Ther.*, 32(5):612–621 (1982).
Weinshilboum et al., *FASEB J.*, 11:3–14 (1997).

* cited by examiner

*Primary Examiner*—Carla J. Myers
(74) *Attorney, Agent, or Firm*—Sheridan Ross P.C.

(57) ABSTRACT

Genetic polymorphisms are identified in the human STP2 gene that alter STP2-dependent drug metabolism. Nucleic acids comprising the polymorphic sequences are used to screen patients for altered metabolism for STP2 substrates, potential drug-drug interactions, and adverse/side effects, as well as diseases that result from environmental or occupational exposure to toxins. The nucleic acids are used to establish animal, cell and in vitro models for drug metabolism.

6 Claims, No Drawings

```
                        SEQUENCE LISTING

<160> NUMBER OF SEQ ID NOS:  110

<210> SEQ ID NO 1
<211> LENGTH: 8396
<212> TYPE: DNA
<213> ORGANISM: H. sapiens

<400> SEQUENCE: 1
ctctccctcc ttgtctctta cctgcctgct gcctgggaca ggatgaagcg gggcccttgt      60
gttgccccaa ccctggctgt tggctaagag cccacgtgat ctgcctgtga gaggagttcc     120
ttccggaaga accagggcag cttctgcccc tagagggcca atgccctagc tgagtgcagt     180
cccccggccc cagcctggtc cagctttggg aagagggtgc ccagttgtgc aatccaggcc     240
ggggcagccg tgtcctgatc ttggtattca gggctgagcc tggagggggc ttgtgatgcc     300
tgactctgtc tctctctctg gccccatgcc ttggtagctg tgaggcgtca ctgctttggg     360
tgacctgatc tggctgtgat ggatgagcac gggggaaata gtggaagact cggaattaga     420
agacgtgagt gggctttggc cccagcctcc ctacccact ccctgtcctg ggctgcctgt      480
gaccaacctt gtttctgcag gcacactgga tagccctgct ggagctcagt gtccctaatc     540
ccctccagat actggtggcc taggggaggt catcaaagac cagtgggaca tcgacctcag     600
cctgtttcca cgtttcttgt tgttttttt tttttgtgga gacagagttt cactcttgtt     660
gcccaggctg gagtgcaatg gcgtgatctt ggctcaccgc aacctctgcc tcccgggttc     720
aagcgattct cctgcctcag cctcccaagt agctgggatt acaggcgtgt gccaccaggc     780
ttgactaatt ttctattttt agtagagaca aggtttctcc atgttggtca ggctggtctc     840
aaactcccga cttcaggtga tctgcctgcc tcggcctccc aaagtgctgg gattacagga     900
gtgagccacc gtgccaggcc ttctccaggc tcttggcacc ttagccagaa acaatttaag     960
```

-continued

```
gacaagtgca aaagtcatga acgtaggcag atttcctgca gagtaaaggg actcactgaa    1020
gaagaggaac gtgggggtcc tcaagagagt gtctcatgcc ctacaaggtg tggggctgac    1080
ctttatgggc ttcttcaact aaagagggt atattcatga agagtccagg aaaaggtaaa    1140
gatttctcaa gaccgtggtg ccacaattta cacccaaata caggtgttcc tggagccgtc    1200
ttggcactgg tgggtgtacg gtttcatatg ttactgattg tacagtgaga tcctaggtga    1260
aacctacatc aaatacagcg ccatgttgct tctggttggt cgcagccagc ttggtcctca    1320
tcctattttt cagggactta ttggcccttg cacatgcag ctatttcaag tttccttctt    1380
ctggtcatgt gaaactgctg cctgggattt tctgttgtct tgctagcact ctattaatct    1440
cacattctcg cctcttttct gtgccacccc ctgctggtcc ggctggtttt cactagagtg    1500
caatacaaag tctcagtcaa gagggcctcc tgaaggttgc tgagggcagg ggtggagcta    1560
gtagccggag gacctgccag tcatggggat tcctcagggg cacagaggag ggaggagggg    1620
cctgtggccc tagcagggga gcagcctctc ctctgcctgg aaatcccatg cctcagtttt    1680
ccccgcttgc ctctgagctc acgcaaccct gggaaggctt gggagactca cctttactca    1740
gatggttgtt tacctgtctc gtgcccagct tgaccctgga cttaaatag tgaggacaaa    1800 gaacgaggag ggtggggga tgcactcctt ccacgggggc ctgtggcttc caagcctcaa    1860
cctcctctgg tctctgtctg tggagcctcc ttcaaaccca tggaaagaaa agtacctgcc    1920
aggggctgtg gttcttctag gatcttctat cgatgttctg tgaggtcccc agggagccat    1980
gaagctgggg ctggctccca gggcaatggg actgcagtgt ccttgttctt tcttgttcta    2040
tggatccatg ctctgctcca cccctgcccc ttcactctgc ccacgcat cactccagac    2100 tggccttgtg gtcagagcct ggagtgcatg ggctgctgga ggcctgtggg ttgcactggg    2160
ccaggacccc tggcaccttc aagactggcc tggagccagc aggtaggtga cctttccagg    2220
gcctgcctat cccagctttc tcctccaatc cctcccctct cttgcctggg tcaattagag    2280
aaagcttgtc ttttggagtt caggggcagg tcaggaccc agtgacagct caaaaaaaaa    2340 acccccaaaaa aaaaaccca ccattgggcc cttttcccctt tcattcttct gttttctaca    2400
caccaaaccc agtcgtggct ttggagatca ctttaagctt gtctccagct ggcaaactaa    2460
ggagggtaat agagaagctc ccccacccc aaccctaccc cttccttccg gaagcaaatc    2520
taagtccagc cccggctcca gatccctccc acactgacct aagaaacccct cagcacagac    2580 aacacccctg cattccccac acaacaccca cactcagcca ctgcgggcga ggagggcacg    2640
aggccaggtt cccaagagct caggtgagtg acacaccgga atggcccagg acgccctcac    2700
cctgctcagc ttgtggctcc aacattccag aagccgaggc ctctgctatc tctgccctct    2760
ccccatggat atcccatttc agacaacccc ggccggcctg aatcccctc ccttccttt    2820 ttttttttccg gggaggccag gtcttgctgt caccgaggct ggagtgctgt gggatcctgg    2880
ccactgcagc cttgaattcc tgggctcaag tgattctcct gcctcagtag ctaggactac    2940
agaccctcac catcctgcct ggatagtttt aaaaaatatt tttaaagat ttttagagat    3000 ggggtcttcc aatgctgccc agattggtct ccaaattctg gcctcagcct ccctagggtc    3060
tgggattaca ggtgggagcc accctgccca ggatcctcct tttgctgagt catcacagtt    3120
ttgctcattc ccacatcagg ctctggcccc caataccagc tcagttgctc aatgggctgt    3180
ttgtcctgga acccagatgg actgtggccg gcaagtgga tcacaggcct ggccagccta    3240
ggagttgcca catgtgaggg gccgaggggc tcaaggaggg gaacatcggg gagaggagcc    3300
```

-continued

```
tactgggtgg aggctggggg tcccagcagg aaatggtgag acaaagggcg ctggctggca   3360
ggaagacagc acaggaaggt cctagaggtt cctcagtgca gctggactct cctggagacc   3420
ttcacacacc ctgacatctg gccccgttc cacgagggtg ctttcactgg tctgcaccat   3480
ggcccaggcc ctgggatttt aacagctcc gcaggtgaat gaaggtgag gccaggctgg     3540
ggaaccacca cattagaacc cgacctggtt ttcagcccca gccccgccac tgactggcct   3600
tgtgagtgcg ggcaagtcac tcaacctccc taggcctcag tgacttccct gaaagcaaga   3660
attccacttt cttgctgttg tgatggtggt aagggaacgg gcctggctct ggcccctgac   3720
gcaggaacat ggagctgatc caggacatct ctcgcccgcc actggagtac gtgaaggggg   3780
tcccgctcat caagtacttt gcagaggcac tgggcccct gcagagcttc caggcccggc    3840
ctgatgacct gctcatcagc acctacccca gtccggtag gtgaggaggg ccacccaccc    3900
tctcccaggt ggcagtcccc accttggcca gcgaggtcat gctcacctca gcctgctcac   3960
ctcccatctc cctccctctc caggcaccac ctgggtgagc cagattctgg acatgatcta   4020
ccagggcgt gacctggaaa agtgtcaccg agctcccatc ttcatgcggg tgcccttcct    4080
tgagttcaaa gtcccaggga ttccctcagg tgtgtgtgtc ctgggtgcaa ggggagtgga   4140
ggaagacagg gctggggctt cagctcacca gaccttccct gacccactgc tcagggatgg   4200
agactctgaa aaacacacca gccccacgac tcctgaagac acacctgccc ctggctctgc   4260
tcccccagac tctgttggat cagaaggtca aggtgagact gggcacagtg gttcacaccc   4320
gcaatctcag tactttggga ggctgaggtg ggaagatccc ttgaagccag aagttccaga   4380
taagtctctt ccaaaaaaaa aacttagctg tgcatagtgg tgtgtgcctg taataccagt   4440
tactcaggag gttgaggtgg gaggatcatc tgagcctagg agtttaaggt tacagcgagc   4500
tatgatcaca ccagtgcact ccaggctggg tgacagagaa acactgtctc aaaaaacgat   4560
gaatagaaag agtgtcccac cagtgcgtg gctcacacct gtaattccag cacttgaaga    4620
ggctgaggca ggtggatcac ctgagactag gagtttgaga tcagcctggc caacatggca   4680
aaaccccatc tctactaaaa atacaaaaaa attagccggg catggtggca ggcatctgta   4740
atcccagcta cttgggaggc tgaagcagga gaattgcttg aagctgggag gcagaggttg   4800
tagtcagccg agacctcacc attgcaccgc agcctgggaa acaagagcaa aactctgtct   4860
caaaaaaaaa agaaaaaaat aaaaagcgg caggtggcag ggggctgggc ctgttgtggc    4920
tcacgcctgt aataccagca cttcggagg tcgaggtggg cagatcaccc aaggttagga    4980
gtttgagatc agtctggcca acatggagaa accccgtctc tactaaaaat acaaaaatta   5040
gccaggcgtt gggcaggcg ccagtaatcc cagctactcg ggaggctgag gaaggagaat    5100
agcttgcacc tgggaggcgg tggttgcagt gagccgagat tgtgccactg tactccagcc   5160
tgggagacac aacgagacat tgtttcaaac aaaacaaata aatattttaa aaggtttgcc   5220
acctgggtgg ctcaccgctg taatgccagc attttgggag gccaagatgg gtggaccgct   5280
tgagctcagg agttccagac cagcccagga acatgggga gactccatct ctataaaaga   5340
tgcaaataat cagcagggca tggtggcata gcgctatagt cccagctact caaaagtcta   5400
aggttggagg attgcttgag cctgggaggt caacgttgca gtgagctatt ctcactccag   5460
tgcactccaa cctgggcaac aggaaaaaag aaagcccaag gtctttttc tcttttctct    5520
ttttttgag acctagagtc ccccccca aaaaaaaaaa aaccacaaca aaagaaaaa       5580
agcaaaggtc caggtgtggg gcatgtgaat ccagggaagg aggccccggc tcagcccagc   5640
tttggtcctg ttcttctggg agagtcgcct cacttcctcc agacttgtct catcttccac   5700
```

```
ggggggact   gtctgccttt   tgctctgatg   accaaaaaca   tgagactctt   ccgggtagac   5760
ctaagaaagg  tagagggtgg   gtcctcacag   acccacaaaa   tttggtggtg   gtgggaacat   5820
gcctggtgga  gcatgccttg   ctccagatcg   gggtgtgacg   cattgatgca   gattatatta   5880
ctatagaata  tgatggtctc   agggaccagg   caggactttg   gcttttgagc   agggttcaga   5940
tcctgacttg  gccctacctg   tgccgtgaga   tctcaaacaa   gtcagcctct   aagcctcagc   6000
ttcctccttt  gccaaaccaa   gagatgagct   ggcctggggc   aggctgtgtg   gtgatggtgc   6060
tggggttgag  tcttctgccc   ctgcaggtgg   tctatgttgc   ccgcaacgca   aaggatgtgg   6120
cggtttccta  ctaccacttc   taccacatgg   ccaaagtgta   ccctcaccct   gggacctggg   6180
aaagcttcct  ggagaagttc   atggctggag   aaggtgggct   tgatgggagg   aaggaaggtg   6240
tggagctaag  gggtggtggc   tacaacgcac   agcaaccctg   tgtcggcacc   cctgcccgc   6300 ttctccagtg  tcctatgggt   cctggtacca   gcacgtgcaa   gagtggtggg   agctgagccg   6360
cacccaccct  gttctctacc   tcttctatga   agacatgaag   gaggtgagac   cgcctttgat   6420
gcttccctcc  acgtgacacc   tgggggcagg   cacttcacag   ggacctgcca   aggccaccca   6480
gccaccctcc  ctgggcggcc   cctccagcag   gcccggattc   cccatcctga   ctccctggcc   6540
caggccccac  tgcagcccca   tgtggcagca   ggctgggcac   agctctcatc   tcctgtgcct   6600
gagtcagctg  cacgggtggc   catggatcag   ctactttttt   ttttgagaca   aagtcttgc   6660 tctgttgtcc  aggatggcat   gcagtggtgt   gatctcagct   cagtgtaacc   ccccctccca   6720
ggttcaagtg  attctcctgc   ctcagcctcc   tgagtagctg   agattacaga   tgcacactac   6780
catgcctggc  taattttgt    gttgtgccat   gttggccagg   ttggtctcca   tctcctgagc   6840
tcaggtgatc  cgcctgcctc   agcctcccaa   agtcttggga   attacacgcc   tgaaccacgg   6900 cccccttgcca cagatcagct   atctattcca   attgcttctc   cctgccaatg   gttatgccac   6960
ccagggccac  aggcacggaa   gaagaccatc   ccagtcctta   cccataggag   ccaagcccag   7020
ctcatgatgg  gatcacaggg   cagacagcaa   ttcattttgc   cccagggact   ggggtcccag   7080
gggtcgagga  gctggctcta   tgggttttga   agtggaagtg   gccagttccc   ctctgaggtt   7140
agagaagtgg  accccttta   ttttcctgaa   tcagcaatcc   aagcctccac   tgaggagccc   7200
tctgctgctc  agaaccccaa   aagggagatt   caaaagatcc   tggagtttgt   ggggcgctcc   7260
ctgccagagg  agactgtgga   cctcatggtt   gagcacacgt   cgttcaagga   gatgaagaag   7320
aaccctatga  ccaactacac   caccgtccgc   cgggagttca   tggaccacag   catctccccc   7380
ttcatgagga  aagtaggtg   ccggccagca   cgggggtttg   gagcaggtgg   gagcagcagc   7440
tggagcctcc  ccataggcac   tcggggcctc   ccctgggatg   agactccagc   tttgctccct   7500
gccttcctcc  cccaggcatg   gctggggact   ggaagaccac   cttccgtg    gcgcagaatg   7560 agcgcttcga  tgcggactat   gcggagaaga   tggcaggctg   cagcctcagc   ttccgctctg   7620
agctgtgaga  ggggttcctg   gagtcactgc   agagggagtg   tgcgaatcaa   gcctgaccaa   7680
gaggctccag  aataaagtat   gatttgtgtt   caatgcagag   tctctattcc   aagccaagag   7740
aaaccctgag  ctgaaagagt   gatcgcccac   tggggccaaa   tacggccacc   tccccgctcc   7800
agctcctcaa  cttgccctgt   ttggagaggg   gagagggtct   ggagaagtaa   aacccaggag   7860
acgagtagag  ggggaatgtg   tttaatccca   gcacgtcctc   tgctgtcctg   ccctgtgtcg   7920 ttggggggatg gcgagtctgc   caggcggcat   cactttttct   tgggttcctt   acaagccacc   7980
acgtatctct  gagccacatt   gaggggaggg   gaatagccat   ctgcataggg   ggtgtcttca   8040
```

-continued

```
aacaggaccg agtagtcatc ctggggctgt ggggcaggca gacaggaggg gctgctcaga    8100 gaccccccagg ccaggacagg cacccccttc ccccagccta gaccacagga ggctctgggc   8160
cgtggactct cagccactcc taacatcctt cactctgggg tcaagaagtc ttggcccagt    8220
ccctgctgct acagagctct tttctcagtg gctggagacc caaggcaggg aataggcagg    8280
gaggagtagg ggtgctgact cccttcctag tggggtcata gctggaggggt ctgctgcctt   8340 tcaaggactc tttgttgaga ggactgaggg caacccagag ggtggcaggc aggggat       8396
```

<210> SEQ ID NO 2
<211> LENGTH: 1396
<212> TYPE: DNA
<213> ORGANISM: H. sapiens
<220> FEATURE:
<221> NAME/KEY: CDS
<222> LOCATION: (426)...(1308)

<400> SEQUENCE: 2

```
gcattcccca cacaacaccc acactcagcc actgcgggcg aggagggcac gaggccaggt     60
tcccaagagc tcaggtttgt cctggaaccc agatggactg tggccgggca agtggatcac   120
aggcctggcc agcctaggag ttgccacatg tgagggggccg aggggctcaa ggaggggaac   180
atcggggaga ggagcctact gggtggaggc tgggggtccc agcaggaaat ggtgagacaa   240
agggcgctgg ctggcaggaa gacagcacag gaaggtccta gaggttcctc agtgcagctg   300
gactctcctg gagaccttca cacacccctga catctgggcc ccgttccacg agggtgcttt   360
cactggtctg caccatggcc caggccctgg gattttgaac agctccgcag gtgaatgaaa   420
```

```
ggaac atg gag ctg atc cag gac atc tct cgc ccg cca ctg gag tac gtg   470
      Met Glu Leu Ile Gln Asp Ile Ser Arg Pro Pro Leu Glu Tyr Val
        1               5                  10                  15 aag ggg gtc ccg ctc atc aag tac ttt gca gag gca ctg ggg ccc ctg    518
Lys Gly Val Pro Leu Ile Lys Tyr Phe Ala Glu Ala Leu Gly Pro Leu
                 20                  25                  30 cag agc ttc cag gcc cgg cct gat gac ctg ctc atc agc acc tac ccc    566
Gln Ser Phe Gln Ala Arg Pro Asp Asp Leu Leu Ile Ser Thr Tyr Pro
             35                  40                  45 aag tcc ggc acc acc tgg gtg agc cag att ctg gac atg atc tac cag    614
Lys Ser Gly Thr Thr Trp Val Ser Gln Ile Leu Asp Met Ile Tyr Gln
         50                  55                  60 ggc ggt gac ctg gaa aag tgt cac cga gct ccc atc ttc atg cgg gtg    662
Gly Gly Asp Leu Glu Lys Cys His Arg Ala Pro Ile Phe Met Arg Val
 65                  70                  75 ccc ttc ctt gag ttc aaa gtc cca ggg att ccc tca ggg atg gag act    710
Pro Phe Leu Glu Phe Lys Val Pro Gly Ile Pro Ser Gly Met Glu Thr
 80                  85                  90                  95 ctg aaa aac aca cca gcc cca cga ctc ctg aag aca cac ctg ccc ctg    758
Leu Lys Asn Thr Pro Ala Pro Arg Leu Leu Lys Thr His Leu Pro Leu
                100                 105                 110 gct ctg ctc ccc cag act ctg ttg gat cag aag gtc aag gtg gtc tat   806
Ala Leu Leu Pro Gln Thr Leu Leu Asp Gln Lys Val Lys Val Val Tyr
            115                 120                 125 gtt gcc cgc aac gca aag gat gtg gcg gtt tcc tac tac cac ttc tac    854
Val Ala Arg Asn Ala Lys Asp Val Ala Val Ser Tyr Tyr His Phe Tyr
        130                 135                 140 cac atg gcc aaa gtg tac cct cac cct ggg acc tgg gaa agc ttc ctg   902
His Met Ala Lys Val Tyr Pro His Pro Gly Thr Trp Glu Ser Phe Leu
145                 150                 155 gag aag ttc atg gct gga gaa gtg tcc tat ggg tcc tgg tac cag cac    950
Glu Lys Phe Met Ala Gly Glu Val Ser Tyr Gly Ser Trp Tyr Gln His
```

```
                                                                              -continued
160                    165                   170                   175
gtg caa gag tgg tgg gag ctg agc cgc acc cac cct gtt ctc tac ctc         998
Val Gln Glu Trp Trp Glu Leu Ser Arg Thr His Pro Val Leu Tyr Leu
                 180                   185                   190 ttc tat gaa gac atg aag gag aac ccc aaa agg gag att caa aag atc         1046
Phe Tyr Glu Asp Met Lys Glu Asn Pro Lys Arg Glu Ile Gln Lys Ile
             195                   200                   205 ctg gag ttt gtg ggg cgc tcc ctg cca gag gag act gtg gac ctc atg         1094
Leu Glu Phe Val Gly Arg Ser Leu Pro Glu Glu Thr Val Asp Leu Met
         210                   215                   220 gtt gag cac acg tcg ttc aag gag atg aag aag aac cct atg acc aac         1142
Val Glu His Thr Ser Phe Lys Glu Met Lys Lys Asn Pro Met Thr Asn
     225                   230                   235 tac acc acc gtc cgc cgg gag ttc atg gac cac agc atc tcc ccc ttc         1190
Tyr Thr Thr Val Arg Arg Glu Phe Met Asp His Ser Ile Ser Pro Phe
240                   245                   250                   255 atg agg aaa ggc atg gct ggg gac tgg aag acc acc ttc acc gtg gcg         1238
Met Arg Lys Gly Met Ala Gly Asp Trp Lys Thr Thr Phe Thr Val Ala
                 260                   265                   270 cag aat gag cgc ttc gat gcg gac tat gcg gag aag atg gca ggc tgc         1286
Gln Asn Glu Arg Phe Asp Ala Asp Tyr Ala Glu Lys Met Ala Gly Cys
             275                   280                   285 agc ctc agc ttc cgc tct gag c tgtgagaggg gttcctggag tcactgcaga          1338
Ser Leu Ser Phe Arg Ser Glu
         290 gggagtgtgc gaatcaagcc tgaccaagag gctccagaat aaagtatgat ttgtgttc         1396

<210> SEQ ID NO 3
<211> LENGTH: 295
<212> TYPE: PRT
<213> ORGANISM: H. sapiens

<400> SEQUENCE: 3

Met Glu Leu Ile Gln Asp Ile Ser Arg Pro Pro Leu Glu Tyr Val Lys
 1               5                  10                   15

Gly Val Pro Leu Ile Lys Tyr Phe Ala Glu Ala Leu Gly Pro Leu Gln
             20                  25                   30

Ser Phe Gln Ala Arg Pro Asp Asp Leu Leu Ile Ser Thr Tyr Pro Lys
         35                  40                   45

Ser Gly Thr Thr Trp Val Ser Gln Ile Leu Asp Met Ile Tyr Gln Gly
     50                  55                   60

Gly Asp Leu Glu Lys Cys His Arg Ala Pro Ile Phe Met Arg Val Pro
 65                  70                  75                   80

Phe Leu Glu Phe Lys Val Pro Gly Ile Pro Ser Gly Met Glu Thr Leu
                 85                  90                   95

Lys Asn Thr Pro Ala Pro Arg Leu Leu Lys Thr His Leu Pro Leu Ala
             100                 105                  110

Leu Leu Pro Gln Thr Leu Leu Asp Gln Lys Val Lys Val Val Tyr Val
         115                 120                  125

Ala Arg Asn Ala Lys Asp Val Ala Val Ser Tyr Tyr His Phe Tyr His
     130                 135                  140

Met Ala Lys Val Tyr Pro His Pro Gly Thr Trp Glu Ser Phe Leu Glu
145                 150                 155                  160

Lys Phe Met Ala Gly Glu Val Ser Tyr Gly Ser Trp Tyr Gln His Val
                 165                 170                  175

Gln Glu Trp Trp Glu Leu Ser Arg Thr His Pro Val Leu Tyr Leu Phe
             180                 185                  190
```

```
Tyr Glu Asp Met Lys Glu Asn Pro Lys Arg Glu Ile Gln Lys Ile Leu
        195                 200                 205

Glu Phe Val Gly Arg Ser Leu Pro Glu Thr Val Asp Leu Met Val
    210                 215                 220

Glu His Thr Ser Phe Lys Glu Met Lys Lys Asn Pro Met Thr Asn Tyr
225                 230                 235                 240

Thr Thr Val Arg Arg Glu Phe Met Asp His Ser Ile Ser Pro Phe Met
                245                 250                 255

Arg Lys Gly Met Ala Gly Asp Trp Lys Thr Thr Phe Thr Val Ala Gln
            260                 265                 270

Asn Glu Arg Phe Asp Ala Asp Tyr Ala Glu Lys Met Ala Gly Cys Ser
        275                 280                 285

Leu Ser Phe Arg Ser Glu Leu
    290                 295
```

<210> SEQ ID NO 4
<211> LENGTH: 18
<212> TYPE: DNA
<213> ORGANISM: H. sapiens

<400> SEQUENCE: 4
cccaaataca ggtgttcc                                                 18

<210> SEQ ID NO 5
<211> LENGTH: 17
<212> TYPE: DNA
<213> ORGANISM: H. sapiens

<400> SEQUENCE: 5
ggagcagagc aaggatc                                                  17

<210> SEQ ID NO 6
<211> LENGTH: 21
<212> TYPE: DNA
<213> ORGANISM: H. sapiens

<400> SEQUENCE: 6
ttcttctagg atcttctatc g                                             21

<210> SEQ ID NO 7
<211> LENGTH: 18
<212> TYPE: DNA
<213> ORGANISM: H. sapiens

<400> SEQUENCE: 7
actcagcaaa aggaggat                                                 18

<210> SEQ ID NO 8
<211> LENGTH: 18
<212> TYPE: DNA
<213> ORGANISM: H. sapiens

<400> SEQUENCE: 8
ttagagatgg ggtcttcc                                                 18

<210> SEQ ID NO 9
<211> LENGTH: 15
<212> TYPE: DNA
<213> ORGANISM: H. sapiens

<400> SEQUENCE: 9
gggcgagaga tgtcc                                              15

<210> SEQ ID NO 10
<211> LENGTH: 17
<212> TYPE: DNA
<213> ORGANISM: H. sapiens

<400> SEQUENCE: 10
ggagaggagc ctactgg                                            17

<210> SEQ ID NO 11
<211> LENGTH: 16
<212> TYPE: DNA
<213> ORGANISM: H. sapiens

<400> SEQUENCE: 11
agtctgaggt gagcat                                             16

<210> SEQ ID NO 12
<211> LENGTH: 17
<212> TYPE: DNA
<213> ORGANISM: H. sapiens

<400> SEQUENCE: 12
gcctcagtga cttccct                                            17

<210> SEQ ID NO 13
<211> LENGTH: 20
<212> TYPE: DNA
<213> ORGANISM: H. sapiens

<400> SEQUENCE: 13
tttggaagag acttatctgg                                         20

<210> SEQ ID NO 14
<211> LENGTH: 16
<212> TYPE: DNA
<213> ORGANISM: H. sapiens

<400> SEQUENCE: 14
gcaggacttt ggcttt                                             16

<210> SEQ ID NO 15
<211> LENGTH: 16
<212> TYPE: DNA
<213> ORGANISM: H. sapiens

<400> SEQUENCE: 15
gactcaggca caggag                                             16

<210> SEQ ID NO 16
<211> LENGTH: 16
<212> TYPE: DNA
<213> ORGANISM: H. sapiens

<400> SEQUENCE: 16
gaccatccca gtcctt                                             16

<210> SEQ ID NO 17
<211> LENGTH: 15
<212> TYPE: DNA
<213> ORGANISM: H. sapiens

```
<400> SEQUENCE: 17
ccccaacgac acagg                                                    15

<210> SEQ ID NO 18
<211> LENGTH: 15
<212> TYPE: DNA
<213> ORGANISM: H. sapiens

<400> SEQUENCE: 18
tggagcccgt cttgg                                                    15

<210> SEQ ID NO 19
<211> LENGTH: 18
<212> TYPE: DNA
<213> ORGANISM: H. sapiens

<400> SEQUENCE: 19
cagcagtttc acttgacc                                                 18

<210> SEQ ID NO 20
<211> LENGTH: 14
<212> TYPE: DNA
<213> ORGANISM: H. sapiens

<400> SEQUENCE: 20
tgccaccccc tgct                                                     14

<210> SEQ ID NO 21
<211> LENGTH: 14
<212> TYPE: DNA
<213> ORGANISM: H. sapiens

<400> SEQUENCE: 21
aggctgctcc cctg                                                     14

<210> SEQ ID NO 22
<211> LENGTH: 14
<212> TYPE: DNA
<213> ORGANISM: H. sapiens

<400> SEQUENCE: 22
gggctcacgc aacc                                                     14

<210> SEQ ID NO 23
<211> LENGTH: 19
<212> TYPE: DNA
<213> ORGANISM: H. sapiens

<400> SEQUENCE: 23
gcaggtactt ttctttcca                                                19

<210> SEQ ID NO 24
<211> LENGTH: 21
<212> TYPE: DNA
<213> ORGANISM: H. sapiens

<400> SEQUENCE: 24
ttcttctagg atcttctatc g                                             21

<210> SEQ ID NO 25
<211> LENGTH: 18
<212> TYPE: DNA
<213> ORGANISM: H. sapiens
```

```
<400> SEQUENCE: 25
tttttgaggt gtcactgg                                                    18

<210> SEQ ID NO 26
<211> LENGTH: 16
<212> TYPE: DNA
<213> ORGANISM: H. sapiens

<400> SEQUENCE: 26
cccacacaac acccac                                                      16

<210> SEQ ID NO 27
<211> LENGTH: 16
<212> TYPE: DNA
<213> ORGANISM: H. sapiens

<400> SEQUENCE: 27
gcttctggaa tgttgg                                                      16

<210> SEQ ID NO 28
<211> LENGTH: 19
<212> TYPE: DNA
<213> ORGANISM: H. sapiens

<400> SEQUENCE: 28
cggaaaaaaa aaaggaag                                                    19

<210> SEQ ID NO 29
<211> LENGTH: 14
<212> TYPE: DNA
<213> ORGANISM: H. sapiens

<400> SEQUENCE: 29
caatgctgcc caga                                                        14

<210> SEQ ID NO 30
<211> LENGTH: 17
<212> TYPE: DNA
<213> ORGANISM: H. sapiens

<400> SEQUENCE: 30
gctccactga ggaacct                                                     17

<210> SEQ ID NO 31
<211> LENGTH: 17
<212> TYPE: DNA
<213> ORGANISM: H. sapiens

<400> SEQUENCE: 31
ggagaggagc ctactgg                                                     17

<210> SEQ ID NO 32
<211> LENGTH: 18
<212> TYPE: DNA
<213> ORGANISM: H. sapiens

<400> SEQUENCE: 32
taccaccatc acaacagc                                                    18

<210> SEQ ID NO 33
<211> LENGTH: 19
<212> TYPE: DNA
```

-continued

```
<213> ORGANISM: H. sapiens

<400> SEQUENCE: 33
ctgaaagcaa gaaatccac                                              19

<210> SEQ ID NO 34
<211> LENGTH: 16
<212> TYPE: DNA
<213> ORGANISM: H. sapiens

<400> SEQUENCE: 34
aggctgaggt gagcat                                                 16

<210> SEQ ID NO 35
<211> LENGTH: 14
<212> TYPE: DNA
<213> ORGANISM: H. sapiens

<400> SEQUENCE: 35
gcggtgacct ggaa                                                   14

<210> SEQ ID NO 36
<211> LENGTH: 20
<212> TYPE: DNA
<213> ORGANISM: H. sapiens

<400> SEQUENCE: 36
tttggaagag acttatctgg                                             20

<210> SEQ ID NO 37
<211> LENGTH: 17
<212> TYPE: DNA
<213> ORGANISM: H. sapiens

<400> SEQUENCE: 37
ctgacttgcc cctacct                                                17

<210> SEQ ID NO 38
<211> LENGTH: 16
<212> TYPE: DNA
<213> ORGANISM: H. sapiens

<400> SEQUENCE: 38
tagccaccac ccctta                                                 16

<210> SEQ ID NO 39
<211> LENGTH: 18
<212> TYPE: DNA
<213> ORGANISM: H. sapiens

<400> SEQUENCE: 39
ccaaagtgta ccctcacc                                               18

<210> SEQ ID NO 40
<211> LENGTH: 14
<212> TYPE: DNA
<213> ORGANISM: H. sapiens

<400> SEQUENCE: 40
agcctgctgc caca                                                   14

<210> SEQ ID NO 41
<211> LENGTH: 16
```

```
<212> TYPE: DNA
<213> ORGANISM: H. sapiens

<400> SEQUENCE: 41
gaccatccca gtcctt                                                      16

<210> SEQ ID NO 42
<211> LENGTH: 14
<212> TYPE: DNA
<213> ORGANISM: H. sapiens

<400> SEQUENCE: 42 caaaccccg tgct                                                         14

<210> SEQ ID NO 43
<211> LENGTH: 18
<212> TYPE: DNA
<213> ORGANISM: H. sapiens

<400> SEQUENCE: 43
ctgtggacct cttggttg                                                    18

<210> SEQ ID NO 44
<211> LENGTH: 22
<212> TYPE: DNA
<213> ORGANISM: H. sapiens

<400> SEQUENCE: 44
cacaaatcat actttattct gg                                               22

<210> SEQ ID NO 45
<211> LENGTH: 15
<212> TYPE: DNA
<213> ORGANISM: H. sapiens

<400> SEQUENCE: 45
cgatgcggac tatgc                                                       15

<210> SEQ ID NO 46
<211> LENGTH: 15
<212> TYPE: DNA
<213> ORGANISM: H. sapiens

<400> SEQUENCE: 46
ccccaacgac acagg                                                       15

<210> SEQ ID NO 47
<211> LENGTH: 22
<212> TYPE: DNA
<213> ORGANISM: H. sapiens

<400> SEQUENCE: 47
ggtgctgggg ttgagtcttc tg                                               22

<210> SEQ ID NO 48
<211> LENGTH: 27
<212> TYPE: DNA
<213> ORGANISM: H. sapiens

<400> SEQUENCE: 48
caaaggatgt ggcggtttcc tactacc                                          27

<210> SEQ ID NO 49
```

```
<211> LENGTH: 23
<212> TYPE: DNA
<213> ORGANISM: H. sapiens

<400> SEQUENCE: 49
acaccttcct tcctcccatc aag                                             23

<210> SEQ ID NO 50
<211> LENGTH: 28
<212> TYPE: DNA
<213> ORGANISM: H. sapiens

<400> SEQUENCE: 50
cgcaaaggat gtggtggttt cctactac                                        28

<210> SEQ ID NO 51
<211> LENGTH: 24
<212> TYPE: DNA
<213> ORGANISM: H. sapiens

<400> SEQUENCE: 51
ggagactgtg gacctcatgg ttga                                            24

<210> SEQ ID NO 52
<211> LENGTH: 32
<212> TYPE: DNA
<213> ORGANISM: H. sapiens

<400> SEQUENCE: 52
tagttggtca tagggttctt cttcatctcc tt                                   32

<210> SEQ ID NO 53
<211> LENGTH: 21
<212> TYPE: DNA
<213> ORGANISM: H. sapiens

<400> SEQUENCE: 53
ccggcaccta cctttcctca t                                               21

<210> SEQ ID NO 54
<211> LENGTH: 30
<212> TYPE: DNA
<213> ORGANISM: H. sapiens

<400> SEQUENCE: 54
tagttggtca tagggtctt cttcatctcc                                       30

<210> SEQ ID NO 55
<211> LENGTH: 21
<212> TYPE: DNA
<213> ORGANISM: H. sapiens

<400> SEQUENCE: 55
agctttgctc cctgccttcc t                                               21

<210> SEQ ID NO 56
<211> LENGTH: 24
<212> TYPE: DNA
<213> ORGANISM: H. sapiens

<400> SEQUENCE: 56
ctgccatctt ctccgcatag tccg                                            24
```

```
<210> SEQ ID NO 57
<211> LENGTH: 22
<212> TYPE: DNA
<213> ORGANISM: H. sapiens

<400> SEQUENCE: 57
ggaacccctc tcacagctca ga                                              22

<210> SEQ ID NO 58
<211> LENGTH: 24
<212> TYPE: DNA
<213> ORGANISM: H. sapiens

<400> SEQUENCE: 58
tgccatcttc ttcgcatagt ccgc                                            24

<210> SEQ ID NO 59
<211> LENGTH: 22
<212> TYPE: DNA
<213> ORGANISM: H. sapiens

<400> SEQUENCE: 59
ggtgctgggg ttgagtcttc tg                                              22

<210> SEQ ID NO 60
<211> LENGTH: 25
<212> TYPE: DNA
<213> ORGANISM: H. sapiens

<400> SEQUENCE: 60
atggccaaag tgtaccctca ccctg                                           25

<210> SEQ ID NO 61
<211> LENGTH: 23
<212> TYPE: DNA
<213> ORGANISM: H. sapiens

<400> SEQUENCE: 61
acaccttcct tcctcccatc aag                                             23

<210> SEQ ID NO 62
<211> LENGTH: 25
<212> TYPE: DNA
<213> ORGANISM: H. sapiens

<400> SEQUENCE: 62
catggccaaa gtgtaaccct caccc                                           25

<210> SEQ ID NO 63
<211> LENGTH: 21
<212> TYPE: DNA
<213> ORGANISM: H. sapiens

<400> SEQUENCE: 63
ccagctcctc aacttgccct g                                               21

<210> SEQ ID NO 64
<211> LENGTH: 21
<212> TYPE: DNA
<213> ORGANISM: H. sapiens

<400> SEQUENCE: 64
ccagctcctc tacttgccct g                                               21
```

<210> SEQ ID NO 65
<211> LENGTH: 21
<212> TYPE: DNA
<213> ORGANISM: H. sapiens

<400> SEQUENCE: 65
gtgagagggg ttcctggagt c				21

<210> SEQ ID NO 66
<211> LENGTH: 21
<212> TYPE: DNA
<213> ORGANISM: H. sapiens

<400> SEQUENCE: 66
gtgagagggg ctcctggagt c				21

<210> SEQ ID NO 67
<211> LENGTH: 21
<212> TYPE: DNA
<213> ORGANISM: H. sapiens

<400> SEQUENCE: 67
catgaagctg gggctggctc c				21

<210> SEQ ID NO 68
<211> LENGTH: 21
<212> TYPE: DNA
<213> ORGANISM: H. sapiens

<400> SEQUENCE: 68
catgaagctg aggctggctc c				21

<210> SEQ ID NO 69
<211> LENGTH: 21
<212> TYPE: DNA
<213> ORGANISM: H. sapiens

<400> SEQUENCE: 69
ctcgtgccca ggttgaccct g				21

<210> SEQ ID NO 70
<211> LENGTH: 21
<212> TYPE: DNA
<213> ORGANISM: H. sapiens

<400> SEQUENCE: 70
ctcgtgccca agttgaccct g				21

<210> SEQ ID NO 71
<211> LENGTH: 21
<212> TYPE: DNA
<213> ORGANISM: H. sapiens

<400> SEQUENCE: 71
gggattcctc agggcacag a				21

<210> SEQ ID NO 72
<211> LENGTH: 21
<212> TYPE: DNA
<213> ORGANISM: H. sapiens

<400> SEQUENCE: 72
gggattcctc cggggcacag a				21

<210> SEQ ID NO 73
<211> LENGTH: 21
<212> TYPE: DNA
<213> ORGANISM: H. sapiens

<400> SEQUENCE: 73
acagcgccat gttgcttctg g                                    21

<210> SEQ ID NO 74
<211> LENGTH: 21
<212> TYPE: DNA
<213> ORGANISM: H. sapiens

<400> SEQUENCE: 74
acagcgccat attgcttctg g                                    21

<210> SEQ ID NO 75
<211> LENGTH: 21
<212> TYPE: DNA
<213> ORGANISM: H. sapiens

<400> SEQUENCE: 75
cagccactgc gggcgaggag g                                    21

<210> SEQ ID NO 76
<211> LENGTH: 21
<212> TYPE: DNA
<213> ORGANISM: H. sapiens

<400> SEQUENCE: 76
cagccactgc aggcgaggag g                                    21

<210> SEQ ID NO 77
<211> LENGTH: 21
<212> TYPE: DNA
<213> ORGANISM: H. sapiens

<400> SEQUENCE: 77
aggagggcac aaggccaggt t                                    21

<210> SEQ ID NO 78
<211> LENGTH: 21
<212> TYPE: DNA
<213> ORGANISM: H. sapiens

<400> SEQUENCE: 78
aggagggcac gaggccaggt t                                    21

<210> SEQ ID NO 79
<211> LENGTH: 21
<212> TYPE: DNA
<213> ORGANISM: H. sapiens

<400> SEQUENCE: 79
ggggaacatc ggggagagga g                                    21

<210> SEQ ID NO 80
<211> LENGTH: 21
<212> TYPE: DNA
<213> ORGANISM: H. sapiens

<400> SEQUENCE: 80

```
ggggaacatc agggagagga g                                        21
```

<210> SEQ ID NO 81
<211> LENGTH: 20
<212> TYPE: DNA
<213> ORGANISM: H. sapiens

<400> SEQUENCE: 81

```
ccaaagtgta ccctcaccct                                          20
```

<210> SEQ ID NO 82
<211> LENGTH: 21
<212> TYPE: DNA
<213> ORGANISM: H. sapiens

<400> SEQUENCE: 82

```
ccaaagtgta accctcaccc t                                        21
```

<210> SEQ ID NO 83
<211> LENGTH: 20
<212> TYPE: DNA
<213> ORGANISM: H. sapiens

<400> SEQUENCE: 83

```
aaggatgtgg ggtttcctac                                          20
```

<210> SEQ ID NO 84
<211> LENGTH: 20
<212> TYPE: DNA
<213> ORGANISM: H. sapiens

<400> SEQUENCE: 84

```
aaggatgtgg ggtttcctac                                          20
```

<210> SEQ ID NO 85
<211> LENGTH: 20
<212> TYPE: DNA
<213> ORGANISM: H. sapiens

<400> SEQUENCE: 85

```
atgaagaaga ccctatgacc                                          20
```

<210> SEQ ID NO 86
<211> LENGTH: 20
<212> TYPE: DNA
<213> ORGANISM: H. sapiens

<400> SEQUENCE: 86

```
atgaagaaga ccctatgacc                                          20
```

<210> SEQ ID NO 87
<211> LENGTH: 20
<212> TYPE: DNA
<213> ORGANISM: H. sapiens

<400> SEQUENCE: 87

```
ggactatgcg agaagatggc                                          20
```

<210> SEQ ID NO 88
<211> LENGTH: 20
<212> TYPE: DNA
<213> ORGANISM: H. sapiens

<400> SEQUENCE: 88
ggactatgcg agaagatggc                          20

<210> SEQ ID NO 89
<211> LENGTH: 21
<212> TYPE: DNA
<213> ORGANISM: H. sapiens

<400> SEQUENCE: 89 aaggggtcc cgctcatcaa g                         21

<210> SEQ ID NO 90
<211> LENGTH: 21
<212> TYPE: DNA
<213> ORGANISM: H. sapiens

<400> SEQUENCE: 90 aaggggtcc tgctcatcaa g                         21

<210> SEQ ID NO 91
<211> LENGTH: 21
<212> TYPE: DNA
<213> ORGANISM: H. sapiens

<400> SEQUENCE: 91
ctctgctatc tctgccctct c                        21

<210> SEQ ID NO 92
<211> LENGTH: 21
<212> TYPE: DNA
<213> ORGANISM: H. sapiens

<400> SEQUENCE: 92
ctctgctatc cctgccctct c                        21

<210> SEQ ID NO 93
<211> LENGTH: 21
<212> TYPE: DNA
<213> ORGANISM: H. sapiens

<400> SEQUENCE: 93
ctctcccagg tggcagtccc c                        21

<210> SEQ ID NO 94
<211> LENGTH: 21
<212> TYPE: DNA
<213> ORGANISM: H. sapiens

<400> SEQUENCE: 94
ctctcccagg cggcagtccc c                        21

<210> SEQ ID NO 95
<211> LENGTH: 20
<212> TYPE: DNA
<213> ORGANISM: H. sapiens

<400> SEQUENCE: 95
cctttgccaa ccaagagatg                          20

<210> SEQ ID NO 96
<211> LENGTH: 19
<212> TYPE: DNA
<213> ORGANISM: H. sapiens

-continued

```
<400> SEQUENCE: 96
cctttgccac caagagatg                                                19

<210> SEQ ID NO 97
<211> LENGTH: 21
<212> TYPE: DNA
<213> ORGANISM: H. sapiens

<400> SEQUENCE: 97
gtgtcggcac tccctgcccg c                                             21

<210> SEQ ID NO 98
<211> LENGTH: 21
<212> TYPE: DNA
<213> ORGANISM: H. sapiens

<400> SEQUENCE: 98
gtgtcggcac ccctgcccg c                                              21

<210> SEQ ID NO 99
<211> LENGTH: 21
<212> TYPE: DNA
<213> ORGANISM: H. sapiens

<400> SEQUENCE: 99
cctccctggg cggcccctcc a                                             21

<210> SEQ ID NO 100
<211> LENGTH: 21
<212> TYPE: DNA
<213> ORGANISM: H. sapiens

<400> SEQUENCE: 100
cctccctggg tggcccctcc a                                             21

<210> SEQ ID NO 101
<211> LENGTH: 21
<212> TYPE: DNA
<213> ORGANISM: H. sapiens

<400> SEQUENCE: 101
ttgttctatg gatccatgct c                                             21

<210> SEQ ID NO 102
<211> LENGTH: 21
<212> TYPE: DNA
<213> ORGANISM: H. sapiens

<400> SEQUENCE: 102
ttgttctatg catccatgct c                                             21

<210> SEQ ID NO 103
<211> LENGTH: 21
<212> TYPE: DNA
<213> ORGANISM: H. sapiens

<400> SEQUENCE: 103
catgggctgc tggaggcctg t                                             21

<210> SEQ ID NO 104
<211> LENGTH: 21
<212> TYPE: DNA
<213> ORGANISM: H. sapiens
```

```
<400> SEQUENCE: 104
catgggctgc cggaggcctg t                                              21

<210> SEQ ID NO 105
<211> LENGTH: 21
<212> TYPE: DNA
<213> ORGANISM: H. sapiens

<400> SEQUENCE: 105
actgggccag gacccctggc a                                              21

<210> SEQ ID NO 106
<211> LENGTH: 21
<212> TYPE: DNA
<213> ORGANISM: H. sapiens

<400> SEQUENCE: 106
actgggccag aacccctggc a                                              21

<210> SEQ ID NO 107
<211> LENGTH: 21
<212> TYPE: DNA
<213> ORGANISM: H. sapiens

<400> SEQUENCE: 107
cctgcctatc ccagctttct c                                              21

<210> SEQ ID NO 108
<211> LENGTH: 21
<212> TYPE: DNA
<213> ORGANISM: H. sapiens

<400> SEQUENCE: 108
cctgcctatc tcagctttct c                                              21

<210> SEQ ID NO 109
<211> LENGTH: 21
<212> TYPE: DNA
<213> ORGANISM: H. sapiens

<400> SEQUENCE: 109
gcctatccca tctttctcct c                                              21

<210> SEQ ID NO 110
<211> LENGTH: 21
<212> TYPE: DNA
<213> ORGANISM: H. sapiens

<400> SEQUENCE: 110
gcctatccca gctttctcct c                                              21
```

GENOTYPING THE HUMAN PHENOL SULFOTRANSFERBASE 2 GENE STP2

This application claims the benefit of U.S. Provisional application 60/088,710, filed Jun. 10, 1998.

Sulfonation is an important pathway in the biotransformation of many drugs, xenobiotics, neurotransmitters, and steroid hormones. Many of the sulfonation reactions for pharmacologic agents are performed by a group of enzymes known as phenol transferases. The phenol sulfotransferase gene family consists to three members located on chromosome 16. A single gene (STM) encodes the thermolabile monoamine-metabolizing form. Two thermostable phenol-metabolizing enzymes are encoded by STP1 and STP2. Substrates for STP1 and STP2 include minoxidil, acetaminophen, and para-nitrophenol. Alterations in phenol sulfotransferase activity have been correlated with individual variation in sulfonation of acetaminophen (Reiter and Weinshilboum (1982) Clin. Pharm.) and predisposition to diet-induced migraine headaches.

The STP2 gene spans approximately 5.1 kb and contains nine exons that range in length from 74 to 347 bp. Exons IA and IB are noncoding and represent two different cDNA 5'-untranslated region sequences. The two apparent 5'-flanking regions of the STP2 gene contain no canonical TATA boxes, but do contain CCAAT elements. STP2 has been localized to human chromosome 16.

Since rates of metabolism of drugs, toxins, etc. can depend on the amounts and kinds of phenol sulfotransferase in tissues, variation in biological response may be determined by the profile of expression of phenol sulfotransferases in each person. Analysis of genetic polymorphisms that lead to altered expression and/or enzyme activity are therefore of interest.

SUMMARY OF THE INVENTION

Genetic sequence polymorphisms are identified in the STP2 gene. Nucleic acids comprising the polymorphic sequences are used in screening assays, and for genotyping individuals. The genotyping information is used to predict an individuals' rate of metabolism for STP2 substrates, potential drug-drug interactions, and adverse/side effects. Specific polynucleotides include the polymorphic STP2 sequences set forth in SEQ ID NOs:63–100.

The nucleic acid sequences of the invention may be provided as probes for detection of STP2 locus polymorphisms, where the probe comprises a polymorphic sequence of SEQ ID NOs:63–110. The sequences may further be utilized as an array of oligonucleotides comprising two or more probes for detection of STP2 locus polymorphisms.

Another aspect of the invention provides a method for detecting in an individual a polymorphism in STP2 metabolism of a substrate, where the method comprises analyzing the genome of the individual for the presence of at least one STP2 polymorphism; wherein the presence of the predisposing polymorphism is indicative of an alteration in STP2 expression or activity. The analyzing step of the method may be accomplished by detection of specific binding between the individual's genomic DNA with an array of oligonucleotides comprising STP2 locus polymorphic sequences. In other embodiments, the alteration in STP2 expression or activity is tissue specific, or is in response to a STP2 modifier that induces or inhibits STP2 expression.

Database References for Nucleotide Sequences

Genbank accession no. U34804 provides the sequence of the STP2 gene.

Brief Description of the Sequence Listing

STP2 Reference Sequences. SEQ ID NO:1 lists the sequence of the reference STP2 gene. The exons are as follows: exon 1A (nt 2591–2664); exon 1B (nt 3180–3526); exon 2 (nt 3726–3877); exon 3 (nt 3985–4110); exon 4 (nt 4196–4293); exon 5 (nt 6088–6214); exon 6 (6310–6404); exon 7 (nt 7214–7394); exon 8 (nt 7517–7712). The mRNA sequence is set forth in SEQ ID NO:2, and the encoded amino acid sequence in SEQ ID NO:3.

Primers. The PCR primers for amplification of polymorphic sequences are set forth as SEQ ID NOs:4–17. The primers used in sequencing isolated polymorphic sequences are presented as SEQ ID NOs:18–46. The primers used in Taqman assays are listed as SEQ ID NO:47–62.

Polymorphisms. Polymorphic sequences of STP2 are presented as SEQ ID NOs:63–110.

DESCRIPTION OF THE SPECIFIC EMBODIMENTS

Pharmacogenetics is the linkage between an individual's genotype and that individual's ability to metabolize or react to a therapeutic agent. Differences in metabolism or target sensitivity can lead to severe toxicity or therapeutic failure by altering the relation between bioactive dose and blood concentration of the drug. Relationships between polymorphisms in metabolic enzymes or drug targets-and both response and toxicity can be used to optimize therapeutic dose administration.

Genetic polymorphisms are identified in the STP2 gene. Nucleic acids comprising the polymorphic sequences are used to screen patients for altered metabolism for STP2 substrates, potential drug-drug interactions, and adverse/side effects, as well as diseases that result from environmental or occupational exposure to toxins. The nucleic acids are used to establish animal, cell culture and in vitro cell-free models for drug metabolism.

Definitions

It is to be understood that this invention is not limited to the particular methodology, protocols, cell lines, animal species or genera, constructs, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a construct" includes a plurality of such constructs and reference to "the STP2 nucleic acid" includes reference to one or more nucleic acids and equivalents thereof known to those skilled in the art, and so forth. All technical and scientific terms used herein have the same meaning as commonly understood to one of ordinary skill in the art to which this invention belongs unless clearly indicated otherwise.

STP2 reference sequence. The sequence of the STP2 gene may be accessed through Genbank as previously cited, and is provided in SEQ ID NO:1 and SEQ ID NO:2 (cDNA sequence). The amino acid sequence of STP2 is listed as SEQ ID NO:3. These sequences provide a reference for the polymorphisms of the invention. The nucleotide sequences provided herein differ from the published sequence at certain positions throughout the sequence. Where there is a discrepancy the provided sequence is used as a reference.

The term "wild-type" may be used to refer to the reference coding sequences of STP2, and the term "variant", or "STP2<sup>v</sup>" to refer to the provided variations in the STP2 sequence. Where there is no published form, such as in the intron sequences, the term wild-type may be used to refer to the most commonly found allele. It will be understood by one of skill in the art that the designation as "wild-type" is merely a convenient label for a common allele, and should not be construed as conferring any particular property on that form of the sequence.

STP2 polymorphic sequences. It has been found that specific sites in the STP2 gene sequence are polymorphic, i.e. within a population, more than one nucleotide (G, A, T, C) is found at a specific position. Polymorphisms may provide functional differences in the genetic sequence, through changes in the encoded polypeptide, changes in mRNA stability, binding of transcriptional and translation factors to the DNA or RNA, and the like. The polymorphisms are also used as single nucleotide polymorphisms to detect association with, or genetic linkage to phenotypic variation in activity and expression of STP2.

SNPs are generally biallelic systems, that is, there are two alleles that an individual may have for any particular marker. SNPs, found approximately every kilobase, offer the potential for generating very high density genetic maps, which will be extremely useful for developing haplotyping systems for genes or regions of interest, and because of the nature of SNPS, they may in fact be the polymorphisms associated with the disease phenotypes under study. The low mutation rate of SNPs also makes them excellent markers for studying complex genetic traits.

Single nucleotide polymorphisms are provided in the STP2 promoter, intron and exon sequences. Table 4 and the corresponding sequence listing provide both forms of each polymorphic sequence. For example, SEQ ID NO:99 and 100 are the alternative forms of a single polymorphic site. The provided sequences also encompass the complementary sequence corresponding to any of the provided polymorphisms.

In order to provide an unambiguous identification of the specific site of a polymorphism, sequences flanking the polymorphic site are shown in Table 4, where the 5' and 3' flanking sequence is non-polymorphic, and the central position, shown in bold, is variable. It will be understood that there is no special significance to the length of non-polymorphic flanking sequence that is included, except to aid in positioning the polymorphism in the genomic sequence. The STP2 exon sequences have been published, and therefore one of each pair of sequences in Table 4 is a publically known sequence.

As used herein, the term "STP2 gene" is intended to generically refer to both the wild-type and variant forms of the sequence, unless specifically denoted otherwise. As it is commonly used in the art, the term "gene" is intended to refer to the genomic region encompassing 5' UTR, exons, introns, and 3' UTR. Individual segments may be specifically referred to, e.g. exon 2, intron 5, etc. Combinations of such segments that provide for a complete STP2 protein may be referred to generically as a protein coding sequence.

Nucleic acids of interest comprise the provided STP2<sup>v</sup> nucleic acid sequence(s), as set forth in Table 4. Such nucleic acids include short hybridization probes, protein coding sequences, variant forms of STP2 cDNA, segments, e.g. exons, introns, etc., and the like. Methods of producing nucleic acids are well-known in the art, including chemical synthesis, cDNA or genomic cloning, PCR amplification, etc.

For the most part, DNA fragments will be of at least 15 nt, usually at least 20 nt, often at least 50 nt. Such small DNA fragments are useful as primers for PCR, hybridization screening, etc. Larger DNA fragments, i.e. greater than 100 nt are useful for production of the encoded polypeptide, promoter motifs, etc. For use in amplification reactions, such as PCR, a pair of primers will be used. The exact composition of primer sequences is not critical to the invention, but for most applications the primers will hybridize to the subject sequence under stringent conditions, as known in the art.

The STP2 nucleic acid sequences are isolated and obtained in substantial purity, generally as other than an intact or naturally occurring mammalian chromosome. Usually, the DNA will be obtained substantially free of other nucleic acid sequences that do not include a STP2 sequence or fragment thereof, generally being at least about 50%, usually at least about 90% pure and are typically "recombinant", i.e. flanked by one or more nucleotides with which it is not normally associated on a naturally occurring chromosome.

For screening purposes, hybridization probes of the polymorphic sequences may be used where both forms are present, either in separate reactions, spatially separated on a solid phase matrix, or labeled such that they can be distinguished from each other. Assays may utilize nucleic acids that hybridize to one or more of the described polymorphisms.

An array may include all or a subset of the polymorphisms listed in Table 4. One or both polymorphic forms may be present in the array, for example the polymorphism of SEQ ID NO:37 and 38 may be represented by either, or both, of the listed sequences. Usually such an array will include at least 2 different polymorphic sequences, i.e. polymorphisms located at unique positions within the locus, and may include as many all of the provided polymorphisms. Arrays of interest may further comprise sequences, including polymorphisms, of other genetic sequences, particularly other sequences of interest for pharmacogenetic screening, e.g. STP1; UGT1, UGT2, cytochrome oxidases, etc. The oligonucleotide sequence on the array will usually be at least about 12 nt in length, may be the length of the provided polymorphic sequences, or may extend into the flanking regions to generate fragments of 100 to 200 nt in length. For examples of arrays, see Ramsay (1998) *Nat. Biotech.* 16:40–44; Hacia et al. (1996) *Nature Genetics* 14:441–447; Lockhart et al. (1996) *Nature Biotechnol.* 14:1675–1680; and De Risi et al. (1996) *Nature Genetics* 14:457–460.

Nucleic acids may be naturally occurring, e.g. DNA or RNA, or may be synthetic analogs, as known in the art. Such analogs may be preferred for use as probes because of superior stability under assay conditions. Modifications in the native structure, including alterations in the backbone, sugars or heterocyclic bases, have been shown to increase intracellular stability and binding affinity. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O- phosphorothioate, 3'-CH2-5'-O-phosphonate and 3'-NH-5'-O-phosphoroamidate. Peptide nucleic acids replace the entire ribose phosphodiester backbone with a peptide linkage.

Sugar modifications are also used to enhance stability and affinity. The a-anomer of deoxyribose may be used, where the base is inverted with respect to the natural b-anomer. The 2'-OH of the ribose sugar may be altered to form 2'-O-methyl or 2'-O-allyl sugars, which provides resistance to degradation without comprising affinity.

Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

STP2 polypeptides. A subset of the provided nucleic acid polymorphisms in STP2 exons confer a change in the corresponding amino acid sequence. Using the amino acid sequence provided in SEQ ID NO:3 as a reference, the amino acid polymorphisms of the invention include pro→leu, pos. 19; ala→val, pos.136; asn→thr, pos. 235; glu→lys, pos 282; and a truncated form resulting from a stop codon at exon 5, position 447. Polypeptides comprising at least one of the provided polymorphisms (STP2$^v$ polypeptides) are of interest. The term "STP2$^v$ polypeptides" as used herein includes complete STP2 protein forms, e.g. such splicing variants as known in the art, and fragments thereof, which fragments may comprise short polypeptides, epitopes, functional domains; binding sites; etc.; and including fusions of the subject polypeptides to other proteins or parts thereof. Polypeptides will usually be at least about 8 amino acids in length, more usually at least about 12 amino acids in length, and may be 20 amino acids or longer, up to substantially the complete protein.

The STP2 genetic sequence, including polymorphisms, may be employed for polypeptide synthesis. For expression, an expression cassette may be employed, providing for a transcriptional and translational initiation region, which may be inducible or constitutive, where the coding region is operably linked under the transcriptional control of the transcriptional initiation region, and a transcriptional and translational termination region. Various transcriptional initiation regions may be employed that are functional in the expression host. The polypeptides may be expressed in prokaryotes or eukaryotes in accordance with conventional ways, depending upon the purpose for expression. Small peptides can also be synthesized in the laboratory.

Substrate. A substrate is a chemical entity that is modified by STP2, usually under normal physiological conditions. Although the duration of drug action tends to be shortened by metabolic transformation, drug metabolism is not "detoxification". Frequently the metabolic product has greater biologic activity than the drug itself. In some cases the desirable pharmacologic actions are entirely attributable to metabolites, the administered drugs themselves being inert. Likewise, the toxic side effects of some drugs may be due in whole or in part to metabolic products.

Substrates of interest may be drugs, xenobiotics, neurotransmitters, steroid hormones, etc. STP2 preferentially catalyzes the sulfonation of 'simple' planar phenols. Substrates include minoxidil, acetaminophen, para-nitrophenol, N-hydroxy 4-aminobiphenyl, etc.

Modifier. A modifier is a chemical agent that modulates the action of STP2, either through altering its enzymatic activity (enzymatic modifier) or through modulation of expression (expression modifier, e.g., by affecting transcription or translation). In some cases the modifier may also be a substrate. Inhibitors include N-ethylmaleimide; phenylglyoxal; 2,6-dichloro-4-nitrophenol; p-nitrophenol; quercetin and other flavonoids, e.g. fisetin, galangin, myricetin, kaempferol, chrysin, apigenin; and phenols such as curcumin, genistein, ellagic acid. Steroids, e.g. estradiol benzoate, testosterone proprionate may affect activity and/or expression.

Pharmacokinetic parameters. Pharmacokinetic parameters provide fundamental data for designing safe and effective dosage regimens. A drug's volume of distribution, clearance, and the derived parameter, half-life, are particularly important, as they determine the degree of fluctuation between a maximum and minimum plasma concentration during a dosage interval, the magnitude of steady state concentration and the time to reach steady state plasma concentration upon chronic dosing. Parameters derived from in vivo drug administration are useful in determining the clinical effect of a particular STP2 genotype.

Expression assay. An assay to determine the effect of a sequence polymorphism on STP2 expression. Expression assays may be performed in cell4ree extracts, or by transforming cells with a suitable vector. Alterations in expression may occur in the basal level that is expressed in one or more cell types, or in the effect that an expression modifier has on the ability of the gene to be inhibited or induced. Expression levels of a variant alleles are compared by various methods known in the art. Methods for determining promoter or enhancer strength include quantitation of the expressed natural protein; insertion of the variant control element into a vector with a reporter gene such as β-galactosidase, luciferase, chloramphenicol acetyltransferase, etc. that provides for convenient quantitation; and the like.

Gel shift or electrophoretic mobility shift assay provides a simple and rapid method for detecting DNA-binding proteins (Ausubel, F. M. et al. (1989) In: Current Protocols in Molecular Biology, Vol. 2, John Wiley and Sons, New York). This method has been used widely in the study of sequence-specific DNA-binding proteins, such as transcription factors. The assay is based on the observation that complexes of protein and DNA migrate through a nondenaturing polyacrylamide gel more slowly than free DNA fragments or double-stranded oligonucleotides. The gel shift assay is performed by incubating a purified protein, or a complex mixture of proteins (such as nuclear or cell extract preparations), with an end-labeled DNA fragment containing the putative protein binding site. The reaction products are then analyzed on a nondenaturing polyacrylamide gel. The specificity of the DNA-binding protein for the putative binding site is established by competition experiments using DNA fragments or oligonucleotides containing a binding site for the protein of interest, or other unrelated DNA sequences.

Expression assays can be used to detect differences in expression of polymorphisms with respect to tissue specificity, expression level, or expression in response to exposure to various substrates, and/or timing of expression during development. For example, since STP2 is expressed in liver, polymorphisms could be evaluated for expression in tissues other than liver, or expression in liver tissue relative to a reference STP2 polypeptide.

Substrate screening assay. Substrate screening assays are used to determine the metabolic activity of a STP2 protein or peptide fragment on a substrate. Many suitable assays are known in the art, including the use of primary or cultured cells, genetically modified cells (e.g., where DNA encoding the STP2 polymorphism to be studied is introduced into the cell within an artificial construct), cell-free systems, e.g. microsomal preparations or recombinantly produced enzymes in a suitable buffer, or in animals, including human clinical trials. Where genetically modified cells are used, since most cell lines do not express STP2 activity (liver cells lines being the exception), introduction of artificial construct for expression of the STP2 polymorphism into many human and non-human cell lines does not require additional modification of the host to inactivate endogenous STP2 expression/activity. Clinical trials may monitor serum, urine, etc. levels of the substrate or its metabolite(s).

Typically a candidate substrate is input into the assay system, and the oxidation to a metabolite is measured over time. The choice of detection system is determined by the substrate and the specific assay parameters. Assays are conventionally run, and will include negative and positive controls, varying concentrations of substrate and enzyme, etc. Exemplary assays may be found in the literature, for examples see Chou et al. (1995) *Carcinogenesis* 16:413–417; Walle and Walle (1991) *Drug Metab. Dispos.* 19:448–453; and Falany et al.. (1990) *Arch. Biochem. Biophys.* 278:312–318.

Genotyping: STP2 genotyping is performed by DNA or RNA sequence and/or hybridization analysis of any convenient sample from a patient, e.g. biopsy material, blood sample (serum, plasma, etc.), buccal cell sample, etc. A nucleic acid sample from an individual is analyzed for the presence of polymorphisms in STP2, particularly those that affect the activity or expression of STP2. Specific sequences of interest include any polymorphism that leads to changes in basal expression in one or more tissues, to changes in the modulation of STP2 expression by modifiers, or alterations in STP2 substrate specificity and/or activity.

Linkage Analysis: Diagnostic screening may be performed for polymorphisms that are genetically linked to a phenotypic variant in STP2 activity or expression, particularly through the use of microsatellite markers or single nucleotide polymorphisms (SNP). The microsatellite or SNP polymorphism itself may not phenotypically expressed, but is linked to sequences that result in altered activity or expression. Two polymorphic variants may be in linkage disequilibrium, i.e. where alleles show non-random associations between genes even though individual loci are in Hardy-Weinberg equilibrium.

Linkage analysis may be performed alone, or in combination with direct detection of phenotypically evident polymorphisms. The use of microsatellite markers for genotyping is well documented. For examples, see Mansfield et al. (1994) *Genomics* 24:225–233; and Ziegle et al. (1992) *Genomics* 14:1026–1031. The use of SNPs for genotyping is illustrated in Underhill et al. (1996) *Proc Natl Acad Sci U S A* 93:196–200.

Transgenic animals. The subject nucleic acids can be used to generate genetically modified non-human animals or site specific gene modifications in cell lines. The term "transgenic" is intended to encompass genetically modified animals having a deletion or other knock-out of STP2 gene activity, having an exogenous STP2 gene that is stably transmitted in the host cells, or having an exogenous STP2 promoter operably linked to a reporter gene. Transgenic animals may be made through homologous recombination, where the STP2 locus is altered. Alternatively, a nucleic acid construct is randomly integrated into the genome. Vectors for stable integration include plasmids, retroviruses and other animal viruses, YACs, and the like. Of interest are transgenic mammals, e.g. cows, pigs, goats, horses, etc., and particularly rodents, e.g. rats, mice, etc.

Genetically Modified Cells. Primary or cloned cells and cell lines are modified by the introduction of vectors comprising STP2 gene polymorphisms. The gene may comprise one or more variant sequences, preferably a haplotype of commonly occurring combinations. In one embodiment of the invention, a panel of two or more genetically modified cell lines, each cell line comprising a STP2 polymorphism, are provided for substrate and/or expression assays. The panel may further comprise cells genetically modified with other genetic sequences, including polymorphisms, particularly other sequences of interest for pharmacogenetic screening, e.g. STP1; UGT1, UGT2, cytochrome oxidases, etc.

Vectors useful for introduction of the gene include plasmids and viral vectors, e.g. retroviral-based vectors, adenovirus vectors, etc. that are maintained transiently or stably in mammalian cells. A wide variety of vectors can be employed for transfection and/or integration of the gene into the genome of the cells. Alternatively, micro-injection may be employed, fusion, or the like for introduction of genes into a suitable host cell.

Genotyping Methods

The effect of a polymorphism in the STP2 gene sequence on the response to a particular substrate or modifier of STP2 is determined by in vitro or in vivo assays. Such assays may include monitoring the metabolism of a substrate during clinical trials to determine the STP2 enzymatic activity, specificity or expression level. Generally, in vitro assays are useful in determining the direct effect of a particular polymorphism, while clinical studies will also detect an enzyme phenotype that is genetically linked to a polymorphism.

The response of an individual to the substrate or modifier can then be predicted by determining the STP2 genotype, with respect to the polymorphism. Where there is a differential distribution of a polymorphism by racial background, guidelines for drug administration can be generally tailored to a particular ethnic group.

The basal expression level in different tissue may be determined by analysis of tissue samples from individuals typed for the presence or absence of a specific polymorphism. Any convenient method may be use, e.g. ELISA, RIA, etc. for protein quantitation, northern blot or other hybridization analysis, quantitative RT-PCR, etc. for mRNA quantitation. The tissue specific expression is correlated with the genotype.

The alteration of STP2 expression in response to a modifier is determined by administering or combining the candidate modifier with an expression system, e.g. animal, cell, in vitro transcription assay, etc. The effect of the modifier on STP2 transcription and/or steady state mRNA levels is determined. As with the basal expression levels, tissue specific interactions are of interest. Correlations are made between the ability of an expression modifier to affect STP2 activity, and the presence of the provided polymorphisms. A panel of different modifiers, cell types, etc. may be screened in order to determine the effect under a number of different conditions.

A STP2 polymorphism that results in altered enzyme activity or specificity is determined by a variety of assays known in the art. The enzyme may be tested for metabolism of a substrate in vitro, for example in defined buffer, or in cell or subcellular lysates, where the ability of a substrate to be metabolized by STP2 under physiologic conditions is determined. Where there are not significant issues of toxicity from the substrate or metabolite(s), in vivo human trials may be utilized, as previously described.

The genotype of an individual is determined with respect to the provided STP2 gene polymorphisms. The genotype is useful for determining the presence of a phenotypically evident polymorphism, and for determining the linkage of a polymorphism to phenotypic change.

A number of methods are available for analyzing nucleic acids for the presence of a specific sequence. Where large amounts of DNA are available, genomic DNA is used directly. Alternatively, the region of interest is cloned into a suitable vector and grown in sufficient quantity for analysis. The nucleic acid may be amplified by conventional techniques, such as the polymerase chain reaction (PCR), to provide sufficient amounts for analysis. The use of the polymerase chain reaction is described in Saiki et al. (1985) *Science* 230:1350–1354, and a review of current techniques may be found in Sambrook et al. Molecular Cloning:. A Laboratory Manual, CSH Press 1989, pp.14.2–14.33. Amplification may be used to determine whether a polymorphism is present, by using a primer that is specific for the polymorphism. Alternatively, various methods are known in the art that utilize oligonucleotide ligation as a means of detecting polymorphisms, for examples see Riley et al. (1990) *Nucleic Acids Res* 18:2887–2890; and Delahunty et al. (1996) *Am J Hum Genet* 58:1239–1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. 32P, 35S, 3H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified or cloned fragment, is analyzed by one of a number of methods known in the art. The nucleic acid may be sequenced by dideoxy or other methods. Hybridization with the variant sequence may also be used to determine its presence, by Southern blots, dot blots,,etc. The hybridization pattern of a control and variant sequence to an array of oligonucleotide probes immobilized on a solid support, as described in U.S. Pat. No. 5,445,934, or in WO95/35505, may also be used as a means of detecting the presence of variant sequences. Single strand conformational polymorphism (SSCP) analysis, denaturing gradient gel electrophoresis (DGGE), mismatch cleavage detection, and heteroduplex analysis in gel matrices are used to detect conformational changes created by DNA sequence variation as alterations in electrophoretic mobility. Alternatively, where a polymorphism creates or destroys a recognition site for a restriction endonuclease (restriction fragment length polymorphism, RFLP), the sample is digested with that endonuclease, and the products size fractionated to determine whether the fragment was digested. Fractionation is performed by gel or capillary electrophoresis, particularly acrylamide or agarose gels.

In one embodiment of the invention, an array of oligonucleotides are provided, where discrete positions on the array are complementary to one or more of the provided polymorphic sequences, e.g. oligonucleotides of at least 12 nt, frequently 20 nt, or larger, and including the sequence flanking the polymorphic position. Such an array may comprise a series of oligonucleotides, each of which can specifically hybridize to a different polymorphism. For examples of arrays, see Hacia et al. (1996) *Nat Genet* 14:441–447 and DeRisi et al. (1996) *Nat Genet* 14:457–460.

The genotype information is used to predict the response of the individual to a particular STP2 substrate or modifier. Where an expression modifier inhibits STP2 expression, then drugs that are a STP2 substrate will be metabolized more slowly if the modifier is co-administered. Where an expression modifier induces STP2 expression, a co-administered substrate will typically be metabolized more rapidly. Similarly, changes in STP2 activity will affect the metabolism of an administered drug. The pharmacokinetic effect of the interaction will depend on the metabolite that is produced, e.g. a prodrug is metabolized to an active form, a drug is metabolized to an inactive form, an environmental compound is metabolized to a toxin, etc. Consideration is given to the route of administration, drug-drug interactions, drug dosage, etc.

Experimental

The following examples are put forth so as to provide those of ordinary skill in the art with a complete disclosure and description of how to make and use the subject invention, and are not intended to limit the scope of what is regarded as the invention.

Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Materials and Methods

DNA samples. Blood specimens from approximately 300 individuals were collected after obtaining informed consent. All samples were stripped of personal identifiers to maintain confidentiality. The only data associated with a given blood sample was gender and self-reported major racial group designations in the United States (Caucasian, Hispanic, African American). Genomic DNA was isolated from these samples using standard techniques. gDNA was either stored as concentrated solutions or stored dried in microtiter plates for future use.

PCR amplifications. The primers used to amplify the coding regions and the promoter region of the STP2 gene from 200 ng of human gDNA are shown in Table 1. Primers were designed based upon publicly available genomic sequence provided by Her et al. (1996) *Genomics* 33:409–420. 100 ng of gDNA from 2 individuals was amplified with the Perkin Elmer GeneAmp PCR kit according to manufacturer's instructions in 100 µl reactions with Taq Gold DNA polymerase, with two exceptions.

Boehringer-Mannheim Expand High Fidelity PCR System kit was used to amplify the promoter region and exon 1A. Magnesium concentrations for each PCR reaction was optimized empirically, and are shown in Table 1.

TABLE 1

PCR primers and AAg++ concentrations.

| Region | Forward/Reverse | SEQ ID | Forward Primer (5' 3') | [AAg++] |
|---|---|---|---|---|
| Promoter | F | 4. | CCCAAATACAGGTGTTCC | 2 mAA |
|  | R | 5. | GGAGCAGAGCAAGGATC |  |
| Exon IA | F | 6. | TTCTTCTAGGATCTTCTATCG | 2 mAA |
|  | R | 7. | ACTCAGCAAAAGGAGGAT |  |
| Exon 1B | F | 8. | TTAGAGATGGGGTCTTCC | 2 mAA |
|  | R | 9. | GGGCGAGAGATGTCC |  |
| Exon 2 | F | 10. | GGAGAGGAGCCTACTGG | 2 mAA |
|  | R | 11. | AGTCTGAGGTGAGCAT |  |
| Exons 3 & 4 | F | 12. | GCCTCAGTGACTTCCCT | 3 mAA |
|  | R | 13. | TTTGGAAGAGACTTATCTGG |  |
| Exons 5 & 6 | F | 14. | GCAGGACTTTGGCTTT | 2 mAA |
|  | R | 15. | GACTCAGGCACAGGAG |  |
| Exons 7 & 8 | F | 16. | GACCATCCCAGTCCTT | 2 mAA |
|  | R | 17. | CCCCAACGACACAGG |  |

Thermal cycling was performed in a GeneAmp PCR System 9600 PCR machine (Perkin Elmer) with an initial denaturation step at 95° C. for 10 min, followed by 35 cycles of denaturation at 95° C. for 30 sec, primer annealing at 60° C. for 45 sec, and primer extension at 72° C. for 2 min, followed by final extension at 72° C. for 5 min, with the following exceptions. 40 cycles were used to amplify exon 1 B and to co-amplify exons 7 and 8. Cycling conditions for the promoter region and exon 1A were an initial denaturation at 95° C. for 2 min, followed by 40 cycles of denaturation at 94° C. for 30 sec, primer annealing at 60° C. for 45 sec, and primer extension at 68° C. for 4 min, followed by a final extension at 68° C. for 7 min.

DNA sequencing. PCR products from 32 individuals, approximately ⅓ from each of the 3 major racial groups (see above), were spin column purified using Microcon-100 columns. Cycle sequencing was performed on the GeneAmp PCR System 9600 PCR machine (Perkin Elmer) using the ABI Prism dRhodamine Terminator Cycle Sequencing Ready Reaction Kit according to the manufacturer's directions. Oligonucleotide primers used for the sequencing reactions are listed in Table 2.

TABLE 2

Sequencing primers.

| Region | Forward/Reverse | SEQ ID | Forward Primer (5' 3') |
|---|---|---|---|
| Promoter (1) | F | 18. | TGGAGCCCGTCTTGG |
|  | R | 19. | CAGCAGTTTCACTTGACC |
| Promoter (2) | F | 20. | TGCCACCCCCTGCT |
|  | R | 21. | AGGCTGCTCCCCTG |
| Promoter (3) | F | 22. | GGGCTCACGCAACC |
|  | R | 23. | GCAGGTACTTTTCTTTCCA |
| Exon 1A (1) | F | 24. | TTCTTCTAGGATCTTCTATCG |
|  | R | 25. | TTTTTGAGGTGTCACTGG |
| Exon IA (2) | F | 26. | CCCACACAACACCCAC |
|  | R | 27. | GCTTCTGGAATGTTGG |
| Exon 1A (3) | R | 28. | CGGAAAAAAAAAAGGAAG |
| Exon 1B (1) | F | 29. | CAATGCTGCCAGA |
|  | R | 30. | GCTCCACTGAGGAACCT |
| Exon 1B (2) | F | 31. | GGAGAGGAGCCTACTGG |
|  | R | 32. | TACCACCATCACAACAGC |

TABLE 2-continued

Sequencing primers.

| Region | Forward/Reverse | SEQ ID | Forward Primer (5' 3') |
|---|---|---|---|
| Exon 2 | F | 33. | CTGAAAGCAAGAAATCCAC |
|  | R | 34. | AGGCTGAGGTGAGCAT |
| Exons 3 & 4 | F | 35. | GCGGTGACCTGGAA |
|  | R | 36. | TTTGGAAGAGACTTATCTGG |
| Exons 5 & 6 (1) | F | 37. | CTGACTTGCCCCTACCT |
|  | R | 38. | TAGCCACCACCCCTTA |
| Exons 5 & 6 (2) | F | 39. | CCAAAGTGTACCCTCACC |
|  | R | 40. | AGCCTGCTGCCACA |
| Exons 7 & 8 (1) | F | 41. | GACCATCCCAGTCCTT |
|  | R | 42. | CAAACCCCCGTGCT |
| Exons 7 & 8 (2) | F | 43. | CTGTGGACCTCTTGGTTG |
|  | R | 44. | CACAAATCATACTTTATTCTGG |
| Exons 7 & 8 (3) | F | 45. | CGATGCGGACTATGC |
|  | R | 46. | CCCCAACGACACAGG |

Eight μl sequencing reactions were subjected to 30 cycles at 96° C. for 20 sec, 50° C. for 20 sec, and 60° C. for 4 min, followed by ethanol precipitation. Samples were evaporated to dryness at 50° C. for ~15 min and resuspended in 2 μl of loading buffer (5:1 deionized formamide:50 mM EDTA pH 8.0), heated to 65° C. for 5 min, and electrophoresed through 4% polyacrylamide/6M urea gels in an ABI 377 Nucleic Acid Analyzer according to the manufacturer's instructions for sequence determination. All sequences were determined from both the 5' and 3' (sense and antisense) direction. Each sequencing reaction was performed with 2 individuals' DNA pooled together. The 16 electropherograms were analyzed by comparing peak heights, looking for ~25% reduction in peak size and/or presence of extra peaks as an indication of heterozygosity. If polymorphisms were identified, pools were subsequently split and resequenced for confirmation.

Population genotyping. High-throughput genotyping using TaqMan technology (ABI) was performed using standard techniques (Livak et al. (1995) PCR Methods and Applications 4:357–362) on the samples described above for 3 STP2 polymorphisms. Oligonucleotide PCR primers and probes used for genotyping are shown in Table 3. Polymorphisms for which allele frequencies were determined are marked with an asterisk (*) in Table 4.

TABLE 3

TaqAAan primers and probes.

| SEQ ID | Description | Primers |
|---|---|---|
| 47. | STP2-136A primer | GGTGCTGGGGTTGAGTCTTCTG |
| 48. | STP2-136Ala probe | CAAAGGATGTGGCGGTTTCCTACTACC |
| 49. | STP2-136B primer | ACACCTTCCTTCCTCCCATCAAG |
| 50. | STP2-136Val probe | CGCAAAGGATGTGGTGGTTTCCTACTAC |
| 51. | STP2-235A primer | GGAGACTGTGGACCTCATGGTTGA |
| 52. | STP2-235Asn probe | TAGTTGGTCATAGGGTTCTTCTTCATCTCCTT |
| 53. | STP2-235B primer | CCGGCACCTACCTTTCCTCAT |

TABLE 3-continued

TaqAAan primers and probes.

| SEQ ID | Description | Primers |
|---|---|---|
| 54. | STP2-235Thr probe | TAGTTGGTCATAGGGGTCTTCTTCATCTCC |
| 55. | STP2-282A primer | AGCTTTGCTCCCTGCCTTCCT |
| 56. | STP2-282Glu probe | CTGCCATCTTCTCCGCATAGTCCG |
| 57. | STP2-282B primer | GGAACCCCTCTCACAGCTCAGA |
| 58. | STP2-282Lys probe | TGCCATCTTCTTCGCATAGTCCGC |
| 59. | STP2-447A primer | GGTGCTGGGGTTGAGTCTTCTG |
| 60. | STP2-DelA447 probe | ATGGCCAAAGTGTACCCTCACCCTG |
| 61. | STP2-447B primer | ACACCTTCCTTCCTCCCATCAAG |
| 62. | STP2-InsA447 probe | CATGGCCAAAGTGTAACCCTCACCC |

Assay name is given by locus and position. Primer names are abbreviated locus-position and letter designations representing forward (A) and reverse (B) primers. Probes are abbreviated locus-position and 3 letter nucleic acid designations representing the nucleic acid alteration in the coding strand of the genomic DNA. Positions at which probes detect nucleic acid variations are shown in bold.

RESULTS

Eight exons, the promoter region, 3' and 5' untranslated regions from the human STP2 gene were resequenced in 32 individuals representing three major ethnic groups (Caucasian, Hispanic, and African American). The polymorphisms are listed in Table 4.

TABLE 4

Newly identified STP2 gene polymorphisms.

| Location; | SEQ ID | Polymorphism Sequence | AA change |
|---|---|---|---|
| 3' end; 99 | 63. | CCAGCTCCTCAACTTGCCCTG | |
| | 64. | CCAGCTCCTCTACTTGCCCTG | |
| 3' TTTR; 7 | 65. | GTGAGAGGGGTTCCTGGAGTC | |
| | 66. | GTGAGAGGGGCTCCTGGAGTC | |
| Promoter; -603 | 67. | CATGAAGCTGGGGCTGGCTCC | |
| | 68. | CATGAAGCTGAGGCTGGCTCC | |
| Promoter; -833 | 69. | CTCGTGCCCAGGTTGACCCTG | |
| | 70. | CTCGTGCCCAAGTTGACCCTG | |
| Promoter; -1005 | 71. | GGGATTCCTCAGGGGCACAGA | |
| | 72. | GGGATTCCTCCGGGGCACAGA | |
| Promoter; -1306 | 73. | ACAGCGCCATGTTGCTTCTGG | |
| | 74. | ACAGCGCCATATTGCTTCTGG | |
| 5' TTTR - A; 36 | 75. | CAGCCACTGCGGGCGAGGAGG | |
| | 76. | CAGCCACTGCAGGCGAGGAGG | |
| 5' TTTR - A; 51 | 77. | AGGAGGGCACAAGGCCAGGTT | |
| | 78. | AGGAGGGCACGAGGCCAGGTT | |
| 5' TTTR - B; 183 | 79. | GGGGAACATCGGGGAGAGGAG | |
| | 80. | GGGGAACATCAGGGAGAGGAG | |
| Exon 5*; 447 | 81. | CCAAAGTGTACCCTCACCCT | INS STOP |
| | 82. | CCAAAGTGTAACCCTCACCCT | INS STOP |
| Exon 5*; 136 (nt 307) | 83. | AAGGATGTGGCGGTTTCCTAC | ALA-VAL |
| | 84. | AAGGATGTGGTGGTTTCCTAC | ALA-VAL |
| Exon 7*; 235 (nt 705) | 85. | ATGAAGAAGAACCCTATGACC | ASN-THR |
| | 86. | ATGAAGAAGACCCCTATGACC | ASN-THR |
| Exon 8*; 282 (nt 845) | 87. | GGACTATGCGGAGAAGATGGC | GLTT-LYS |
| | 88. | GGACTATGCGAAGAAGATGGC | GLTT-LYS |
| Exon 2; 19 (nt 56) | 89. | AAGGGGGTCCCGCTCATCAAG | PRO-LETT |
| | 90. | AAGGGGGTCCTGCTCATCAAG | PRO-LETT |
| Intron 1A; 88 | 91. | CTCTGTTATCTCTGCCCTCTC | |
| | 92. | CTCTGTTATCCCTGCCCTCTC | |
| Intron 2; 34 | 93. | CTCTCCCAGGTGGCAGTCCCC | |
| | 94. | CTCTCCCAGGCGGCAGTCCCC | |
| Intron 4; -71 | 95. | CCTTTGCCAACAAGAGATG | DEL A |
| | 96. | CCTTTGCCAACAAGAGATG | DEL A |
| Intron 5; -19 | 97. | GTGTCGGCACTCCCTGCCCGC | |
| | 98. | GTGTCGGCACCCCCTGCCCGC | |
| Intron 6; 93 | 99. | CCTCCCTGGGCGGCCCCTCCA | |
| | 100. | CCTCCCTGGGTGGCCCCTCCA | |
| Promoter; -547 | 101. | TTGGTCTATGGATCCATGCTC | |
| | 102. | TTGGTCTATGCATCCATGCTC | |
| Promoter; -453 | 103. | CATGGGCTGCTGGAGGCCTGT | |
| | 104. | CATGGGCTGCCGGAGGCCTGT | |
| Promoter; -425 | 105. | ACTGGGCCAGGACCCCTGGCA | |
| | 106. | ACTGGGCCAGAACCCCTGGCA | |
| Promoter; -358 | 107. | CCTGCCTATCCCAGCTTTCTC | |
| | 108. | CCTGCCTATCTCAGCTTTCTC | |
| Promoter; -355 | 109. | GCCTATCCCATCTTTCTCCTC | |
| | 110. | GCCTATCCCAGCTTTCTCCTC | |

Genotyping of 95 individuals from each of 3 broadly defined racial groups (African Americans, Hispanic Americans, and Caucasian Americans) for three polymorphisms produced the allele and genotype frequencies shown in Table 5.

TABLE 5

Allele and Genotype Population Frequencies. Polymorphism name includes gene abbreviation followed by nucleotide designation for allele 1, then nucleotide number, then nucleotide designation for allele 2. Population abbreviations are as follows: AfAm = African Americans; BAH = Caucasians from the United States; Cauc = Caucasians from California; Hisp = Hispanics from California. Allele names are designated by nucleotide and position. Genotypes are designated by position and 2 nucleotides representing each of the chromosomes in a given individual.

| Locus Calc Name | Start Position | Population | Allele Freq | Genotype Freq |
|---|---|---|---|---|
| STP2 STP2_Ala136Val_AfAm | 0 | African Americans, California | STP2_Ala136 = 0.997<br>STP2_Val136 = 0.003 | STP2_136Ala/Ala = 0.995<br>STP2_136Ala/Val = 0.005<br>STP2_136Val/Val = 0 |
| STP2 STP2_Ala136Val_Cauc2 | 0 | Caucasion, USA | STP2_Ala136 = 1<br>STP2_Val136 = 0 | STP2_136Ala/Ala = 1<br>STP2_136Ala/Val = 0<br>STP2_136Val/Val = 0 |
| STP2 STP2_Ala136Val_Cauc | 0 | Caucasion, California | STP2_Ala136 = 1<br>STP2_Val136 = 0 | STP2_136Ala/Ala = 1<br>STP2_136Ala/Val = 0<br>STP2_136Val/Val = 0 |
| STP2 STP2_Ala136Val_Chin | 0 | Chinese, California | STP2_Ala136 = 1<br>STP2_Val136 = 0 | STP2_136Ala/Ala = 1<br>STP2_136Ala/Val = 0<br>STP2_136Val/Val = 0 |
| STP2 STP2_Ala136Val_Hisp | 0 | Hispanics, California | STP2_Ala136 = 1<br>STP2_Val136 = 0 | STP2_136Ala/Ala = 1<br>STP2_136Ala/Val = 0<br>STP2_136Val/Val = 0 |
| STP2 STP2_Ala136Val_Japn | 0 | Japanese, California | STP2_Ala136 = 1<br>STP2_Val136 = 0 | STP2_136Ala/Ala = 1<br>STP2_136Ala/Val = 0<br>STP2_136Val/Val = 0 |
| STP2 STP2_insA447_AfAm | 0 | African Americans, California | STP2_delA447 = 0.981<br>STP2_insA447 = 0.019 | STP2_447delA/delA = 0.963<br>STP2_447delA/insA = 0.007<br>STP2_447insA/insA = 0 |
| STP2 STP2_insA447_Cauc2 | 0 | Caucasion, USA | STP2_delA447 = 1<br>STP2_insA447 = 0 | STP2_447delA/delA = 1<br>STP2_447delA/insA = 0<br>STP2_447insA/insA = 0 |
| STP2 STP2_insA447_Cauc | 0 | Caucasion, California | STP2_delA447 = 1<br>STP2_insA447 = 0 | STP2_447delA/delA = 1<br>STP2_447delA/insA = 0<br>STP2_447insA/insA = 0 |
| STP2 STP2_insA447_Chin | 0 | Chinese, California | STP2_delA447 = 1<br>STP2_insA447 = 0 | STP2_447delA/delA = 1<br>STP2_447delA/insA = 0<br>STP2_447insA/insA = 0 |
| STP2 STP2_insA447_Hisp | 0 | Hispanics, California | STP2_delA447 = 0.995<br>STP2_insA447 = 0.005 | STP2_447delA/delA = 0.989<br>STP2_447delA/insA = 0.011<br>STP2_447insA/insA = 0 |
| STP2 STP2_insA447_Japn | 0 | Japanese, California | STP2_delA447 = 1<br>STP2_insA447 = 0 | STP2_447delA/delA = 1<br>STP2_447delA/insA = 0<br>STP2_447insA/insA = 0 |
| STP2 STP2_Asn235Thr_AfAm | 0 | African Americans, California | STP2_Asn235 = 0.749<br>STP2_Thr235 = 0.251 | STP2_235Asn/Asn = 0.562<br>STP2_235Asn/Thr = 0.373<br>STP2_235Thr/Thr = 0.065 |
| STP2 STP2_Asn235Thr_Cauc2 | 0 | Caucasion, USA | STP2_Asn235 = 0.753<br>STP2_Thr235 = 0.247 | STP2_235Asn/Asn = 0.565<br>STP2_235Asn/Thr = 0.376<br>STP2_235Thr/Thr = 0.059 |
| STP2 STP2_Asn235Thr_Cauc | 0 | Caucasion, California | STP2_Asn235 = 0.649<br>STP2_Thr235 = 0.351 | STP2_235Asn/Asn = 0.42<br>STP2_235Asn/Thr = 0.458<br>STP2_235Thr/Thr = 0.122 |
| STP2 STP2_Asn235Thr_Chin | 0 | Chinese, California | STP2_Asn235 = 0.934<br>STP2_Thr235 = 0.066 | STP2_235Asn/Asn = 0.882<br>STP2_235Asn/Thr = 0.105<br>STP2_235Thr/Thr = 0.013 |
| STP2 STP2_Asn235Thr_Hisp | 0 | Hispanic, California | STP2_Asn235 = .623<br>STP2_Thr235 = 0.377 | STP2_235Asn/Asn = 0.385<br>STP2_235Asn/Thr = 0.476<br>STP2_235Thr/Thr = 0.139 |
| STP2 STP2_Asn235Thr_Japn | 0 | Japanese, California | STP2_Asn235 = 0.855<br>STP2_Thr235 = 0.145 | STP2_235Asn/Asn = 0.75<br>STP2_235Asn/Thr = 0.211<br>STP2_235Thr/Thr = 0.039 |
| STP2 STP2_Glu282Lys_AfAm | 0 | African Americans, California | STP2_Glu282 = 0.949<br>STP2_Lys282 = 0.051 | STP2_282Glu/Glu = 0.899<br>STP2_282Glu/Lys = 0.101<br>STP2_282Lys/Lys = 0 |
| STP2 STP2_Glu282Lys_Cauc2 | 0 | Caucasion, USA | STP2_Glu282 = 1<br>STP2_Lys282 = 0 | STP2_282Glu/Glu = 1<br>STP2_282Glu/Lys = 0<br>STP2_282Lys/Lys = 0 |
| STP2 STP2_Glu282Lys_Cauc | 0 | Caucasion, California | STP2_Glu282 = 0.997<br>STP2_Lys282 = 0.003 | STP2_282Glu/Glu = 0.995<br>STP2_282Glu/Lys = 0.005<br>STP2_282Lys/Lys = 0 |
| STP2 STP2_Glu282Lys_Chin | 0 | Chinese, California | STP2_Glu282 = 1<br>STP2_Lys282 = 0 | STP2_282Glu/Glu = 1<br>STP2_282Glu/Lys = 0<br>STP2_282Lys/Lys = 0 |
| STP2 STP2_Glu282Lys_Hisp | 0 | Hispanic, California | STP2_Glu282 = 0.992<br>STP2_Lys282 = 0.008 | STP2_282Glu/Glu = 0.984<br>STP2_282Glu/Lys = 0.016<br>STP2_282Lys/Lys = 0 |
| STP2 STP2_Glu282Lys_Japn | 0 | Japanese, California | STP2_Glu282 = 1 | STP2_282Glu/Glu = 1 |

TABLE 5-continued

Allele and Genotype Population Frequencies. Polymorphism name includes gene abbreviation followed by nucleotide designation for allele 1, then nucleotide number, then nucleotide designation for allele 2. Population abbreviations are as follows: AfAm = African Americans; BAH = Caucasians from the United States; Cauc = Caucasians from California; Hisp = Hispanics from California. Allele names are designated by nucleotide and position. Genotypes are designated by position and 2 nucleotides representing each of the chromosomes in a given individual.

| Locus Calc Name | Start Position | Population | Allele Freq | Genotype Freq |
|---|---|---|---|---|
| | | | STP2_Lys282 = 0 | STP2_282Glu/Lys = 0 |
| | | | | STP2_282Lys/Lys = 0 |

Each of the polymorphisms identified in this study are unique and newly described. Several of the nucleotide base changes result in amino acid changes that may alter enzyme activity by any of a number of possible mechanisms. The changes in the 5' and 3' UTRs may alter regulation of transcription or transcript stability. Promoter region alterations may result in altered regulation or efficiency of transcription.

All of these polymorphisms have utility. As the human genome project progresses, polymorphisms within every human gene must be identified in order to perform whole genome association studies that will be necessary for identifying genetic etiologies of complex diseases. These polymorphisms are useful for association studies.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated STP2 polynucleotide comprising a nucleic acid sequence selected from the group consisting of:
   (a) a nucleic acid sequence comprising at least 12 contiguous nucleotides of a nucleic acid sequence selected from the group consisting of SEQ ID NO:68, SEQ ID NO:70, SEQ ID NO:72, SEQ ID NO:74, SEQ ID NO:76, SEQ ID NO:77, SEQ ID NO:82, SEQ ID NO:84, SEQ ID NO:88, SEQ ID NO:96, SEQ D NO:97, SEQ ID NO:100, SEQ ID NO:102, SEQ ID NO:104, SEQ ID NO:108, and SEQ ID NO:109,
   (b) a nucleic acid sequence comprising at least 50 contiguous nucleotides and comprising a nucleic acid sequence selected from the group consisting of SEQ ID NO:80, and SEQ ID NO:106;
   (c) a nucleic acid sequence comprising at least 100 contiguous nucleotides and comprising a nucleic acid sequence of SEQ ID NO:102; and,
   (d) a nucleic acid sequence that is fully complementary to a nucleic acid sequence of (a), (b), or (c).

2. An isolated STP2 polynucleotide according to claim 1, wherein the polynucleotide is a nucleic acid probe for the detection of STP2 locus polymorphisms.

3. An isolated STP2 polynucleotide according to claim 2, wherein said polynucleotide is conjugated to a detectable marker.

4. An array of polynucleotides comprising:
two or more isolated polynucleotides comprising at least one STP2 polynucleotide of claim 1.

5. A method for detecting in an individual a STP2 polynucleotide, the method comprising:
  (a) obtaining a nucleic acid sample that has been isolated from an individual; and
  (b) contacting said nucleic acid sample with a STP2 polynucleotide probe, wherein said STP2 polynucleotide probe comprises a nucleic acid sequence selected from the group consisting
    (i) a nucleic acid sequence comprising at least 12 contiguous nucleotides of a nucleic acid sequence selected from the group consisting of SEQ ID NO:68, SEQ ID NO:70, SEQ D) NO:72, SEQ ID NO:74, SEQ ID NO:76, SEQ ID NO:77, SEQ ID NO:82, SEQ ID NO:84, SEQ ID NO:88, SEQ ID NO:96, SEQ ID NO:97, SEQ ID NO:100, SEQ ID NO:102, SEQ ID NO:104, SEQ ID NO:108, and SEQ ID NO:109;
    (ii) a nucleic acid sequence comprising at least 50 contiguous nucleotides and comprising a nucleic acid sequence selected from the group consisting of SEQ ID NO:80, and SEQ ID NO:106;
    (iii) a nucleic acid sequence comprising at least 100 contiguous nucleotides and comprising a nucleic acid sequence of SEQ ID NO:102; and,
    (iv) a nucleic acid sequence that is fully complementary to a nucleic acid sequence of (i)–(iii); and,
  (c) detecting specific hybridization between said polynucleotide probe and said nucleic acid sample as indicative of the presence of a STP2 polynucleotide in said nucleic acid sample.

6. A method according to claim 5, wherein said detecting step comprises detecting hybridization between sad nucleic acid sample with an array of polynucleotides comprising:
two or more isolated polynucleotides comprising at least one STP2 polynucleotide probe of claim 5.

* * * * *